(12) United States Patent
Pallen et al.

(10) Patent No.: US 7,199,121 B2
(45) Date of Patent: Apr. 3, 2007

(54) PROTEIN TYROSINE PHOSPHATASE INHIBITOR

(75) Inventors: Catherine J. Pallen, Singapore (SG); Haishan Wang, Singapore (SG); Kah Leong Lim, Singapore (SG); Su Ling Yeo, Singapore (SG); Yue Wang, Singapore (SG); Yin Hwee Tan, Singapore (SG)

(73) Assignee: Institute of Molecular and Cell Biology, Singapore (SG)

( * ) Notice: Subject to any disclaimer, the term of this patent is extended or adjusted under 35 U.S.C. 154(b) by 231 days.

(21) Appl. No.: 10/363,914

(22) PCT Filed: Sep. 7, 2001

(86) PCT No.: PCT/CA01/01285

§ 371 (c)(1),
(2), (4) Date: Apr. 29, 2003

(87) PCT Pub. No.: WO02/20525

PCT Pub. Date: Mar. 14, 2002

(65) Prior Publication Data

US 2004/0138218 A1    Jul. 15, 2004

(30) Foreign Application Priority Data

Sep. 8, 2000    (GB) ................................ 0022079.8

(51) Int. Cl.
- C07D 487/04 (2006.01)
- A61K 31/53 (2006.01)
- A61P 35/00 (2006.01)
- A61P 31/10 (2006.01)

(52) U.S. Cl. ....................... 514/243; 544/184
(58) Field of Classification Search ............... 544/184; 514/243
See application file for complete search history.

(56) References Cited

FOREIGN PATENT DOCUMENTS

EP    0 407 888    1/1991

OTHER PUBLICATIONS

Cecil Textbook of Medicine, edited by Bennet, J.C., and Plum F., 20th edition,vol. 1, 1004-1010, 1996.*
Zhang et al. Expert Opin. Investig. Drugs 12 (2)223-233, 2003.*
by Brown et al. Australian Journal of Chemistry, 27(8): 1781-1790, 1974.*
Ichiba et al. Journal of Organic Chemistry 43(3): 469-472, 1978.*
Taylor et al. Journal of Organic Chemistry 40(16): 2321-2329, 1975.*
Taylor and Sowinski, "Structure and Total Synthesis of the Pyrimido . . . ", Journal of the American Chemical Society 1969, 91, 2143-2144.

Azez and Aleksandrov, "Products of Interaction of Fervenulin-3-One-4-Oxide With o-Phenylenediamines", Khimiko-Farmatsevticheskii Zhurnal 34(9):39-41 (2000).
Azev et al, "Synthesis and Some Pharmacological Properties of Isofervenulin Derivatives", Khimiko-Farmatsevticheskii Zhurnal 14(4):39-44 (1980).
Mel'nik et al, "Synthesis of Glycosidic Derivatives of Reumycin", Database Biosys 'Online! Biosciences Information Service, Philadelphia, PA, Database Accession No. PREV198375004578, XP002186274 & Bioorganicheskaya Khimiya 7(11):1723-1730 (1981).
Andersen et al, "2-(Oxalylamino)-Benzoic Acid Is a General, Competitive Inhibitor of Protein-tyrosine Phosphatases", The Journal of Biological Chemistry 275(10):7101-7108 (2000).

* cited by examiner

*Primary Examiner*—Venkataraman Balasubramanian
(74) *Attorney, Agent, or Firm*—Nixon & Vanderhye P.C.

(57) ABSTRACT

Use of a compound of formula (I):

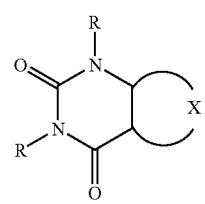

(I)

wherein
each R, which are the same or different, is H or $C_1$–$C_6$ alkyl, and
X completes a ring which is a substituted triazine having one of the following formulae (II) to (IV):

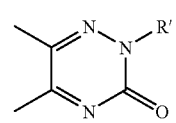

(II)

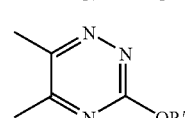

(III)

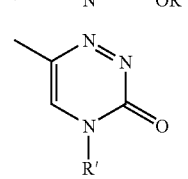

(IV)

wherein R' is H or $C_1$–$C_6$ alkyl;
or an enol tautomer of a compound of formula (I) in which any of the groups R or R' is hydrogen;
in the manufacture of a medicament for use as a protein tyrosine phosphatase (PTP) inhibitor. Formula (I) embraces 2-methylfervenulone, which can be produced by fermentation of a novel microbial strain. Fermentation of the said strain also produces novel precursors to 2-methylfervenulone having utility as prodrugs.

8 Claims, No Drawings

PROTEIN TYROSINE PHOSPHATASE INHIBITOR

This application is the US national phase of international application PCT/CA01/01285, filed 7 Sep. 2001, which designated the US.

The present invention relates to the use of 2-methylfervenulone and structurally related compounds as protein tyrosine phosphatase (PTP) inhibitors and their use in the treatment of diseases or disorders mediated by protein tyrosine phosphatases, in particular cancer and type II diabetes. It also relates to the production of 2-methylfervenulone and novel diastereomeric precursors thereto by the fermentation of a novel microbial strain, and to the use of the precursors as prodrugs for 2-methylfervenulone.

Covalent modification by tyrosine phosphorylation is a major mechanism for regulating the functions of proteins involved in multiple aspects of cellular, physiological and pathogenic processes. It is reversibly controlled through the dynamic actions of protein tyrosine kinases (PTKs) and phosphatases (PTPs). Numerous and specific inhibitors of PTKs have been isolated and tested as therapeutic agents against human diseases. In addition, the large diversity of the PTP superfamily and the demonstrated roles of several PTPs as positive regulators of cellular signalling pathways and in certain human diseases, indicates that these phosphatases are also promising targets for therapeutic manipulation.

PTPs may be more fully termed as protein tyrosine phosphate phosphohydrolases. They may be divided into three classes based on their structural organisation. Class I contains the non-receptor molecules possessing a single catalytic domain (for example PTP IB, TCPTP, SHP-2). Class II and III PTPases are receptor-like transmembrane proteins. Class II contains PTPs with a single cytoplasmic catalytic domain such as PTPβ (HPTPβ). Class III members are LCA, LAR, HPTPα, HPTPγ, HPTPδ, HPTPε, DPTP, DLAR and possess two repeated putative catalytic domains in the cytoplasmic region of the molecule.

It has been found that over-expression of the receptor-like human PTPα (HPTPα) results in persistent activation of pp60$^{c-src}$. The kinase activity of pp60$^{c-src}$ is specifically and transiently increased during cell mitosis and repressed during interphase. Loss of cell cycle control of pp60$^{c-src}$ occurs upon mutation of Tyr 527 to Phe or when pp60$^{c-src}$ is associated with polyoma middle-T-antigen, and these conditions result in cell transformation or tumourigenesis. This indicates that PTPα may function as an oncogene. An inhibitor of PTPα is therefore of use in the treatment of a tumour exhibiting an elevated level of pp60$^{c-src}$ kinase activity.

PTP inhibitors may be used to treat a tumour exhibiting an elevated level of pp60$^{c-src}$ kinase activity. Any tumour which has abnormally active or overactive pp60$^{c-src}$, which may be a result of PTPα overexpression or overactivation in the tumour, may be treated. The tumour may be a tumour with increased pp60$^{c-src}$ activity which cannot be accounted for by a proportional increase in pp60$^{c-src}$ amount. Such tumours include human colon carcinoma, rhabdomyosarcoma, osteogenic sarcoma and Ewing's sarcoma. In particular inhibitors may be used in the treatment of human colon carcinoma which is the third most common human malignancy. The inhibitors may therefore be used in the treatment of colorectal cancer.

Protein tyrosine phosphatases are also associated with type II diabetes (Non-insulin Dependent Diabetes Mellitus (NIDDM)). NIDDM is one of the most common metabolic disorders ill the industrial world. Associated with the disorder are dyslipidemias, atherosclerosis, hypertension, cardiovascular disorders and renal dysfunction. Two physiological defects that lead to the development of diabetes are tissue resistance to the effects of insulin and altered secretion of insulin.

Some PTP inhibitors are known. These include zinc ions, vanadates such as sodium orthovanadate and arsenites such as phenylarsine oxide. These compounds are, however, fairly toxic. The present invention seeks to provide alternative PTP inhibitors which may have reduced toxicity.

It has now been found that fermentation of a strain of *Streptomyces* sp. in a nutrient medium produces a metabolite which is active in a PTP inhibitory assay. The metabolite has been identified as 2-methylfervenulone, also referred to hereinafter as compound 3. This compound and closely related structural analogues thereof may be used as inhibitors of PTP.

Accordingly the present invention provides the use of a compound of formula (I):

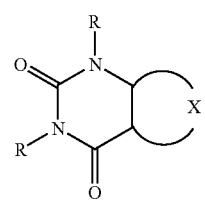

(I)

wherein each R, which are the same or different, is H or $C_1$–$C_6$ alkyl, and

X completes a ring which is a substituted triazine having one of the following formulae (II) to (IV):

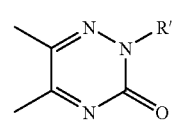

(II)

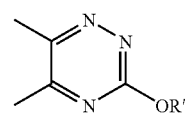

(III)

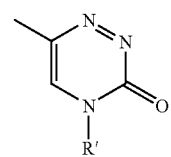

(IV)

wherein R' is H or $C_1$–$C_6$ alkyl;

or an enol tautomer of a compound of formula (I) in which any of the groups R or R' is hydrogen;

in the manufacture of a medicament for use as a protein tyrosine phosphatase (PTP) inhibitor.

In a preferred embodiment the compound has the following formula (Ia):

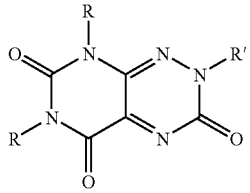

wherein R and R' are as defined above.

A $C_1$–$C_6$ alkyl group may be, for instance, $C_1$–$C_4$ alkyl such as methyl, ethyl, i-propyl, n-propyl, s-butyl, t-butyl, n-butyl or i-butyl. In formulae (I) and (Ia) R and R', which are the same or different, are preferably selected from hydrogen, methyl and ethyl. In a particularly preferred embodiment each of R and R' in formula (I) or (Ia) is the same. Most preferably each of R and R' is methyl.

When each of R and R' in formula (I) is methyl the compound is 2-methylfervenulone when X is a ring of formula (II) as defined above and is a methyl isomer of 2-methylfervenulone when X is a ring of formula (III) or (IV) as defined above. The compound of formula (Ia) is 2-methylfervenulone when each of R and R' is methyl. 2-methylfervenulone is 2,8-dihydro-2,6,8-trimethyl-pyrimido[5,4-e]-1,2,4-triazine-3,5,7(6H)-trione.

Tautomerism can arise when any of R and R' in formula (I) or (Ia) as defined above is hydrogen. Thus, when there is an NH group at the α-position relative to a carbonyl group the compound can exist as either the keto tautomer or the enol tautomer. In practice one tautomer tends to be more stable than the other and therefore predominates. All the chemical structures are depicted herein in the keto form, but the enol tautomers are also embraced within the scope of the present invention.

The compounds of formula I are known compounds and can be synthesised by methods described in the literature or by appropriate modifications of such syntheses using conventional techniques. For instance, the synthesis of 2-methylfervenulone and its methyl isomers is described by Taylor and Sowinski in Journal of the American Chemical Society 1969, 91, 2143–2144. The 2-methylfervenulone obtained synthetically as described in this document was identical with the naturally occurring compound both in physical properties (melting point, mixture melting point; nmr, uv, and ir spectra; tlc) and in biological properties. The processes described by Taylor and Sowinski may be adapted by known methodologies to obtain other compounds of formula (I) in which R and R' are H or $C_1$–$C_6$ alkyl other than methyl.

In the present invention 2-methylfervenulone was identified as a PTP inhibitor by high-throughput screening of actinomycete extracts. It was isolated from an extract of a microorganism which has been designated IM 2096 and which was identified as a strain of the genus *Streptomyces* on the basis of the taxonomy data described in the Example below.

The microbial strain *Streptomyces* sp. IM 2096 was deposited by the Institute of Molecular and Cell Biology of 30 Medical Drive, Singapore 117609, Singapore, under the Budapest Treaty at the Agricultural Research Service Culture Collection (NRRL), in Ill., USA on 24th August 2000. The deposited strain was assigned the reference number NRRL 30334.

Fermentation of microbial strain IM 2096 also produces the novel compound 4a-(2-amino-5-oxo-4,5-dihydro-3H-imidazol-4-yl)-2,4,4a,8-tetrahydro-2,6,8-trimethyl-pyrimido[5,4-e]-1,2,4-triazine-3,5,7(6H)-trione which exists as two diastereomers, referred to below as compounds 1 and 2. Compounds 1 and 2 degrade on storage to 2-methylfervenulone. They therefore have utility as prodrugs of 2-methylfervenulone and, as such, form another aspect of the present invention.

Accordingly, the present invention further provides 4a-(2-amino-5-oxo-4,5-dihydro-3H-imidazol-4-yl)-2,4,4a,8-tetrahydro-2,6,8-trimethyl-pyrimido[5,4-e]-1,2,4-triazine-3,5,7(6H)-trione or an acid addition salt thereof. This trione is of formula (V):

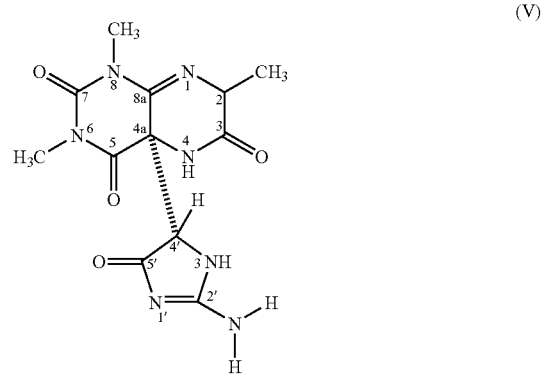

As mentioned above and discussed in the Example which follows, formula (V) exists in two diastereomeric forms. These are compounds 1 and 2, which can interconvert due to the acidic 4'-H which permits epimerisation to occur easily. As a result, the two chiral centres 4a and 4' in the above structural formula are not assigned.

Compounds 1 and 2 slowly decompose to 2-methylfervenulone, compound 3. They can therefore be formulated in a pharmaceutical composition and administered to a patient as prodrugs of 2-methylfervenulone. Accordingly, the present invention further provides the use of a trione of formula (V) as defined above, or an acid addition salt thereof, as a prodrug for 2-methylfervenulone. A pharmaceutical composition comprising a pharmaceutically acceptable carrier or diluent and a trione of formula (V) as defined above, or an acid addition salt thereof, is also provided.

The present invention further provides a process for the preparation of a compound which is 2-methylfervenulone or 4a-(2-amino-5-oxo-4,5-dihydro-3H-imidazol-4-yl)-2,4,4a,8-tetrahydro-2,6,8-trimethyl-pyrimido[5,4-e]-1,2,4-triazine-3,5,7(6H)-trione, which process comprises.

(i) fermenting, in a source of carbon, nitrogen and inorganic salts, strain *Streptomyces* sp IM 2096 (NRRL 30334) or a mutant thereof which produces a said compound; and
(ii) isolating a said compound from the fermentation broth.

If desired, 4a-(2-amino-5-oxo-4,5-dihydro-3H-imidazol-4-yl)-2,4,4a,8-tetrahydro-2,6,8-trimethyl-pyrimido[5,4-e]-1,2,4-triazine-3,5,7(6H)-trione may be converted into an acid addition salt thereof. For instance, suitable salts include salts with inorganic or organic acids. The trifluoroacetic acid (TFA) salt is particularly preferred.

As indicated, the present invention also embraces the use of mutants of the above microorganism. For example, those which are obtained by natural selection or those produced by mutating agents including ionising radiation such as ultra-violet radiation, or chemical mutagens such as nitrosoguanidine or the like treatments, are also included within the ambit of this invention.

The invention further provides a biologically pure culture of Streptomyces sp. IM 2096 or of a mutant thereof which produces 2-methylfervenulone and 4a-(2-amino-5-oxo-4,5-dihydro-3H-imidazol-4-yl)-2,4,4a,8-tetrahydro-2,6,8-trimethyl-pyrimido[5,4-e]-1,2,4-triazine-3,5,7(6H)-trione. Such cultures are substantially free from other microorganisms. The invention also provides a process for fermenting Streptomyces sp. strain IM 2096 or a said mutant, which process comprises fermenting Streptomyces sp. IM 2096 or a said mutant thereof in a source of carbon, nitrogen and inorganic salts.

Assimilable sources of carbon, nitrogen and minerals may be provided by either simple or complex nutrients. Sources of carbon will generally include glucose, maltose, starch, glycerol, molasses, dextrin, lactose, sucrose, fructose, carboxylic acids, amino acids, glycerides, alcohols, alkanes and vegetable oils. Sources of carbon will generally comprise from 0.5 to 10% by weight of the fermentation medium.

Sources of nitrogen will generally include soya bean meal, corn steep liquors, distillers' solubles, yeast extracts, cottonseed meal, peptones, ground nut meal, malt extract, molasses, casein, amino acid mixtures, ammonia (gas or solution), ammonium salts or nitrates. Urea and other amides may also be used. Sources of nitrogen will generally form from 0.1 to 10% by weight of the fermentation medium.

Nutrient mineral salts which may be incorporated into the culture medium include the generally used salts capable of yielding sodium, potassium, ammonium, iron, magnesium, zinc, nickel, cobalt, manganese, vanadium, chromium, calcium, copper, molybdenum, boron, phosphate, sulphate, chloride and carbonate ions.

An antifoam may be present to control excessive foaming and added at intervals as required.

Fermentation can be conducted at temperatures ranging from 20° C. to 40° C., preferably at about 30° C., for one day to two weeks, preferably for about 7 days.

The separation of 2-methylfervenulone and the diastereomers of 4a-(2-amino-5-oxo-4,5-dihydro-3H-imidazol-4-yl)-2,4,4a,8-tetrahydro-2,6,8-trimethyl-pyrimido[5,4-e]-1,2,4-triazine-3,5,7(6H)-trione from the fermentation broth and their recovery is carried out by solvent extraction followed by application of chromatographic fractionations with various chromatographic techniques and solvent systems. The compounds in pure form have thus been isolated in this way.

Compounds of formula (I) are PTP inhibitors. A bioassay demonstrating the PTP inhibitory activity of 2-methylfervenulone is described in the Example which follows. A patient in need of a PTP inhibitor may therefore be treated with a compound of formula (I), or an enol tautomer thereof, as defined above. The condition of the patient may thereby be improved. Accordingly, the invention provides a method of treating a patient in need of PTP inhibitor which method comprises the administration thereto of a therapeutically effective amount of a compound of formula (I) or enol tautomer thereof as defined above.

In accordance with the present invention a medicament comprising a compound of formula I or enol tautomer thereof as defined above is used to treat a PTP mediated disease or disorder. For example, a compound of formula I may be used to treat a tumour, in particular a tumour with increased $pp60^{c-src}$ activity. Examples of tumours which the compounds may be used to treat therefore include human colon carcinoma, rhabdomyosarcoma, osteogenic sarcoma, and Ewing's sarcoma, in particular human colon carcinoma. In particular a compound of formula I, or a medicament containing it, may be used in the treatment of colorectal cancer.

If desired, a compound of formula (I) or a tautomer thereof, as defined above, may be used as an antitumour agent according to a combined chemotherapy regimen. Thus, in one embodiment the invention provides the use of a compound of formula (I) or a tautomer thereof, as defined above, in the manufacture of a medicament for administration in combination with an additional chemotherapeutic agent. For instance, the medicament can be administered in combination with an additional chemotherapeutic agent selected from taxane, taxane derivatives, CPT-11, camptothecin derivatives, anthracycline glycosides, e.g. doxorubicin or epirubicin, etoposide, navelbine, vinblastine, carboplatin, cisplatin and the like, optionally within liposomal formulations thereof. In one embodiment the medicament itself further comprises the said additional chemotherapeutic agent.

The invention also provides a product comprising a compound of formula I and one or more chemotherapeutic agents selected from taxane, taxane derivatives, CPT-11, camptothecin derivatives, anthracycline glycosides, etoposide, navelbine, vinblastine, carboplatin and cisplatin as a combined preparation for simultaneous, separate or sequential administration in the treatment of a tumour. Such a combined preparation may, for instance, be used for treating colorectal cancer.

In another embodiment of the present invention the medicament comprising a compound of formula I may be used in the treatment of type II diabetes.

The invention further provides a method of treatment of cancer which method comprises administering to a patient in need thereof an effective amount of a compound of formula (I) as defined above. The method of treatment preferably administered compound of formula (Ia) as defined above. The compound of formula (I) is preferably 2-methylfervenulone or a methyl isomer thereof. Cancers which may be treated using the method of the invention include human colon carcinoma, rhabdomyosarcoma, osteogenic sarcoma or Ewing's sarcoma. In the method of the invention, the compound of formula (I) is suitably administered in combination therapy with an additional chemotherapeutic agents selected taxane, taxane derivatives CPT-11, camptothecin derivatives, anthracycline glycosides, etoposide, navelbine, vinblastine, carboplatin and cisplatin.

The invention further provides a method of treatment of type II diabetes which comprises administering to a patient in need thereof an effective amount of compound of formula (I) as defined above. The compound is preferably a compound of formula (Ia) as defined above, more preferably 2-methylfervenulone or a methyl isomer thereof.

A suitable dosage of a compound of formula I is typically from 0.1 to 30 mg/kg body weight of the subject to be treated per day. A preferred dosage range is from 1 to 20 mg/kg.

The compounds of formula I and the 2-methylfervenulone prodrugs of formula V, and the salts thereof, can be administered in a variety of dosage forms, e.g. orally, in the form of tablets, capsules, sugar- or film-coated tablets, liquid solutions or suspensions; rectally, in the form of suppositories; or parenterally, e.g. intramuscularly, or by intravenous injection or infusion.

The dosage regimen for the compounds and/or compositions containing the above compounds is based on a variety of factors, including the type, age, weight, sex and medical condition of the patient; the severity of the condition; the route of administration; and the activity of the particular compound employed. Thus the dosage regime may vary widely.

In one embodiment of the invention the said compounds are formulated for intravenous use. As such, the formulations can be administered to patients either as a slow injection, e.g. over about 30 minutes to about 3 hours, or as a bolus injection, also referred to as IV (intravenous) push.

The parenteral formulations of the present invention are prepared according to conventional techniques adopted in the preparation of pharmaceutical forms for parenteral use. Typically an appropriate amount of a compound of formula I or enol tautomer thereof, or a prodrug of formula V either as a dry powder or in a lyophilised form, is dissolved in a pharmaceutically acceptable solution for parenteral use. As an example, a compound of formula I or formula V is dissolved in a suitable amount of sterile water or aqueous dextrose solution, e.g. 5% dextrose in water for intravenous administration. The above mixture is then stirred, sterilised, and subsequently lyophilised according to conventional techniques. The freeze-dried formulation is prepared and stored in vials for injection; the addition of an appropriate amount of sterile water or a physiological solution for parenteral use enables the preparation of the final formulation to be injected.

The above method is also suitable for preparing high dosage formulations of a compound of formula I or formula V. The unit-strength of the formulation to be injected depends on the concentration of the active agent in the solution itself and, of course, on the filling volume of the vials used to prepare the final formulation.

The solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example by means of mixing, granulating, tabletting, sugar-coating or film-coating processes.

The liquid solution for oral administration may be, e.g., syrups, emulsions and suspensions. The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose or polyvinyl alcohol.

The suppositories may contain, together with the active compound, a pharmaceutically acceptable carrier, e.g. cocabutter, polyethylene glycol, a polyoxyethylene sorbitan fatty acid ester surfactant or lecithin.

The formulations comprising a compound of formula I or a prodrug of formula V may optionally contain additional pharmaceutically acceptable excipients for parenteral administration such as, for instance, bulking agents, e.g. lactose or mannitol, pH buffering agents, anti-oxidant agents, preservative agents, tonicity adjusters and the like.

The present invention is further illustrated in the following Example.

EXAMPLE 1

Isolation and Testing of 2-methylfervenulone

General Experimental Procedure

TLC was carried out on precoated plates: analytical (Merck Kieselgel 60 $F_{254}$), spots visualized with UV light; preparative-scale (Aldrich, silica, 1 mm thick). Flash column chromatography was performed with silica (Merck, 70–230 and 230–400 mesh). Optical rotations were measured with a JASCO DIP-1000 Digital Polarimeter. Infrared spectra (IR) were recorded with a Perkin-Elmer 1600 Series FTIR (film or KBr pellet). All the 1D and 2D NMR experiments for $^1H$ (400.13 MHz), $^{13}C$ (100.61 MHz) and $^{15}N$ (40.55 MHz) nuclei were obtained on a Bruker AVANCE-400 digital NMR spectrometer. $^1H$—$^{13}C$ and $^1H$—$^{15}N$ 2D experiments (HMQC, HSQC and HMBC) were run with Z-gradient selection. $^1H$ and $^{13}C$ chemical shifts are expressed in ppm relative to internal tetramethylsilane, $^{15}N$ (40.55 MHz) chemical shifts were obtained from 2D experiments and are calibrated with 80% $MeNO_2$ in $CDCl_3$ as 380.2 ppm. HRMS spectra were determined using a VG Micromass 7035E instrument (EI) and a PerSeptive Biosystems Mariner TOF spectrometer (ESI). Analytical HPLC was performed on a Hewlett-Packard 1050Ti series equipped with a diode array detector, using a $C_{18}$ column (ODS Hypersil, 5 μm, 4.6×250 mm) and linear gradient elution (flow rate, 1.0 mL/min; solvent A, 0.1% TFA in water; solvent B, 0.1% TFA in MeOH; solvent B increased from 5% to 60% in 20 min and then from 60% to 100% in additional 5 min).

*Actinomycetes* Extract:

Approximately two thousand different strains of *Actinomycetes* were fermented in 6 different types of 10 mL liquid media for 7 days at 30° C. Each culture with its cells and supernatant was extracted by adding an equal amount of 100% methanol and incubating overnight at 30° C. The extracts were filtered and the filtrates freeze dried in 2 mL aliquots for long term storage at −70° C.

High-throughput Screens: (HTS)

HTS for inhibitory activity towards PTPα was performed in 96 well plates (Nunclon). Dephosphorylation of the substrate (pNPP) was measured in 180 μL reactions/well in assay buffer containing 50 mM sodium acetate (pH 5.5), 0.5 mg/mL BSA and 0.5 mM dithiothreitol. The purified enzyme PTPα (0.3 μg/well) and extracts (5 μL in 50% methanol) were preincubated for 5–10 min at room temperature in a volume of 170 μl. Reactions were initiated by adding 10 μL of substrate in assay buffer to a final concentration of 2 mM. For each plate, 6 reference control wells containing PTPα were preincubated with 5 μL 50% methanol at the same time as the test samples. As a positive control for PTPα inhibition, 1 μM $Na_3VO_4$, a potent inhibitor of PTPs, was added to some wells. Blank wells contained 5 μL 50% methanol, 2 mM pNPP in assay buffer and no enzyme. For each set of experiments (from 2–5 plates), reference controls in a separate plate were read at different time points to check the linearity of the reaction. Reactions were stopped with 25 μL $KH_2PO_4$ after 45–60 mins incubation at room temperature. The plates were read immediately in a multilabel counter (Wallac 1420 Victor). The OD$_{405}$ of the reference wells ranged between 0.7–1.2, which represents <10% conversion of the substrate and falls within the linear part of the reaction. Percentage inhibition was determined using the formula:

% Inhibition=[{(OD ref–OD blank)–(OD test–OD blank)}/(OD ref–OD blank)]×100

Phosphatase Assay:

The expression, purification, quantitation and storage of bacterially expressed PTPα, PTPε, and PTPβ have been described in the literature. All other PTPs described in the text were purchased from New England Biolabs. Dephosphorylation of pNPP was measured in 450 μL reactions containing 50 mM sodium acetate (pH 5.5, or pH 7 for CIP), 0.5 mg/mL BSA, 0.5 μM dithiothreitol, and 2 mM pNPP. Reactions with IPP also contained 2 mM Mn$^{2+}$. The RR-src peptide was phosphorylated, and used at 2.5 μM in reactions with PTPα. All reactions were carried out at 30° C. and terminated during the linear portion of the reaction.

Microtitre plate-based screening demonstrated that the compounds of formula (I) inhibited para-nitrophenyl phosphate (pNPP) and phosphotyrosyl RR-src peptide dephosphorylation by >70% and >60%, respectively. One extract from the fermentation broth of IM 2096 reproducibly exerted >60% inhibition of PTPα and on other PTPs subsequently tested, including TCPTP, LAR, PTPβ, and PTPε (data not shown). This extract was selected for further purification.

Isolation and Taxonomy of the Actinomycete Strain IM 2096

The procedures for the isolation and taxonomic characterization of the strain IM 2096 were as described by Wang et al. (*Industrial Microbiol. Biotech* 1999, 23, 178–187) The actinomycete strain IM 2096, from which 3 was purified, was isolated from a soil sample collected in the Singapore Botanic Garden. Its colony exhibits properties characteristic of Streptomyces on ISP 4 medium plate. Both aerial and substrate mycelia were well developed. At maturity straight chains with more than 20 spores were formed on the aerial mycelium. The colour of the aerial mycelium was white and that of the substrate mycelium was light brown. No diffusible pigment was produced on ISP 2, ISP 3, ISP 4 and Bennett medium plates. The cell wall peptidoglycan contained a major amount of L-diaminopimelic acid. The complete nucleotide sequence of the 16S rRNA gene of IM 2096 was determined for phylogenetic analysis. IM 2096 was found to have the closest phylogenetic relationship with *Streptomyces albulus*, and the 16S rRNA gene sequences are 97% identical between the two organisms. On the basis of morphological, chemotaxonomic and phylogenetic evidences, we assigned the actinomycete strain IM 2096 to the genus Streptomyces.

Purification Procedure

The bioassay active fermentation broth (4 L) was freeze-dried. The solid residue was extracted with MeOH (2.5 L×2), 10% H$_2$O in MeOH (2 L×2) and 20% H$_2$O in MeOH (1 L×3) at room temperature. The bioassay active extracts were combined and concentrated under reduced pressure below 35° C. The wet residue (about ⅓ of the total) was first mixed with silica gel (70–230 mesh) and freeze-dried then applied on a silica gel (230–400 mesh) column. The column (internal diameter, 6 cm; sample layer height, 4.5 cm; fine silica layer, 6 cm) was eluted with ethyl acetate in hexanes (0%, 250 mL; 50%, 250 mL; 100%, 250 mL×2), MeOH in CH$_2$Cl$_2$ (0%, 250 mL×2; 50%, 250 mL×2; 90%, 250 mL×2; 100%, 250 mL×3), 10% H$_2$O in MeOH (250 mL×2). The active fractions (usually the 10% to 90% MeOH in CH$_2$Cl$_2$) were combined and evaporated below 30° C. under reduced pressure.

The above residue was further fractionated either by a semi-preparative Waters 600E system equipped with a 990 photodiode array detector (PDA), using a Prep Nova-Pak HRC$_{18}$ column (6 μm, 7.8 mm×300 mm, flow rate 2 mL/min, solvent MeOH/water) or by a Waters Delta Prep 4000 system equipped with a 996 photodiode array detector, using Prep Nova-Pak HRC$_{18}$ column segments (6 μm, 25 mm×310 mm; flow rate, 21.2 mL/min; solvent A=water, B=MeOH; 0–5 min, 5% B, 5–30 min, 5% to 30% B, linear gradient, 30–40 min, 100% B). Fractions corresponding to different peaks were freeze-dried. Two of them were found active in the bioassay. These were labelled 1 (105 mg, overall yield from the 4 L of fermentation broth) and 2 (73 mg).

Identification of Compounds Extracted

The isolated 1 and 2 were unstable and contained ca 6%-10% of 3 by HPLC analysis. The latter could be removed and isolated by simply washing 1 and 2 with CH$_2$Cl$_2$. 1 and 2 could also be further purified by HPLC (25 mm×310 mm column, flow rate, 20 mL/min, MeOH/Water containing 0.1% TFA) to give their TFA salts. The purification also provided a yellow fraction (mainly 3) and a polar fraction which was confirmed as glycocyamidine by MS (ESI).

Crude 3 obtained from washing 1 and 2 with CH$_2$Cl$_2$ and HPLC fraction was purified by preparative TLC (silica, ethyl acetate/MeOH/CH$_2$Cl$_2$=30:9:1, developed twice) to give 3 (12 mg) and 4 (5 mg).

1 and 2 did not contain any sulfur (by MS) or phosphorous (by $^{31}$P NMR). They have the same nominal molecular weight (ESI, M+H=323) and this was further confirmed by LC/MS. Their NMR spectra were very similar, therefore, only the interpretation of the spectra of 1 (see Table 1) is discussed in the following text. The $^1$H NMR of 1 in DMSO-d$_6$ showed four active proton signals at δ 8.02, 7.85, 7.46, 7.17 and four non-exchangeable singlets at δ 4.05 (1H), 3.06 (3H), 3.09 (3H) and 3.12 (3H). No cross peak was found in the COSY experiment. The $^{13}$C NMR and DEPT spectra suggested 1 has 11 carbons: 3 methyl groups, one methine, one quaternary carbon and other 6 quaternary carbons in the range of amide or amidine type carbons (Table 1). The $^1$H—$^{13}$C HMQC experiment assigned the CH$_3$ and CH signals. Connectivity of the partial structure was established by $^1$H—$^{13}$C HMBC experiment (optimal J=6 Hz) cross-peaks [N2-CH$_3$ (δ 3.12)/C-3 (δ 149.4), C-8a (δ 134.8, weak); N8-CH$_3$ (δ 3.09)/C-7 (δ 149.6) and C-8a (δ 134.8); N6-CH$_3$ (δ 3.06)/C-7 (δ 149.6) and C-5 (δ 164.3); H-4' (δ 4.05)/C-5' (δ 182.8), C-2' (δ 172.9), C-5 (δ 164.3), C-8a (δ 134.8) and C-4a (δ 60.6); H-4 (δ 7.46)/C-8a (δ 134.8) and C-4a (δ 60.6).

As the NMR information obtained from $^1$H and $^{13}$C nuclei was not enough to provide the entire connectivity, $^1$H—$^{15}$N HSQC and HMBC experiments were performed. The HSQC spectra showed two cross-peaks [H-4 (δ 7.46)/N-4 (δ 81.3); H-3' (δ 8.02)/N-3' (δ 84.7)], the other two active protons provided no cross-peak as they were too broad. The HMBC experiments (optimal J=8 and 4 Hz) showed more cross-peaks [H-4' (δ 4.05)/N-4 (δ 81.3); N2-CH$_3$ (δ 3.12)/N-1 (δ 285.3) and N-2 (δ 130.9); N8-CH$_3$ (δ 3.09)/N-8 (δ 108.7); N6-CH$_3$ (δ 3.06)/N-6 (δ 143.9). $^{15}$N peak at δ 285.3 suggested the existence of a pyridine-like nitrogen (=N—).

Clearly compound 1 has a structure of a two-ring system with a side chain. As the molecular weight of 1 is an even number (322) with the possible formula suggested to be $C_{11}H_{14}N_{6+x}O_y$, only X=2 with Y=4 satisfies the requirement. HRMS (ESI) further confirmed the formula $C_{11}H_{14}N_8O_4$ (M+H, m/z 323.1222, calcd for $C_{11}H_{15}N_8O_4$, 323.1216). The two "invisible" nitrogen atoms not detected in the NMR spectra are most likely to be in the side chain, which has the formula $C_3H_5N_3O$. Among all the possible structures derived from the formula $C_3H_5N_3O$, glycocyamidine (5) is the best match with respect to the NMR data. In order to confirm the structure of 1, the TFA salt of 1 was farther investigated. The $^1H$—$^{13}C$ and $^1H$—$^{15}N$ HSQC experiments of the TFA salt of 1 gave more connectivity information than that of the free base. With optimal J=2 Hz, the $^1H$—$^{13}C$ HMBC showed good correlation through 4, 5, even 6 bonds; the 1H—$^{15}N$ HMBC experiments also showed very important correlations through $^3J$ and $^4J$. 1 and 2 have similar NMR spectra and data. 2 is the diastereomer of 1, and they can interconvert. This is due to the acidic 4'-H which causes epimerization to occur easily. As a result, the two chiral centers at C-4a and C-4' are not assigned.

1 and 2 are soluble in DMSO, methanol and water, but insoluble in dichloromethane, chloroform and hexanes. They are unstable in solutions (water, MeOH, DMSO). They slowly decompose to a yellow fluorescent compound. After washing the partially decomposed 1 and 2 with $CH_2Cl_2$, the yellow fraction was separated from 1 and 2. The crude yellow fraction was purified by preparative TLC to give 3 and 4.

The formula of 3 was confirmed as $C_8H_9N_5O_3$ by HRMS (EI) (m/z calcd 223.0705; found 223.0713, −3.6 ppm) or by HRMS (ESI) [m/z calcd for $C_8H_{10}N_5O_3$ (M+H), 224.0784; found, 224.0787). Its NMR data is listed in Table 3. Its structure was elucidated using the combination of $^1H$, $^{13}C$ NMR; $^1H$—$^{13}C$ HMQC, HMBC and $^1H$—$^{15}N$ HMBC experiments. 3 was confirmed to be 2-methylfervenulone.

The formula of 4 was confirmed as $C_7H_9N_5O_2$ by HRMS (EI) (m/z calcd 195.0756; found, 195.0756). Its structure was also elucidated by a combination of $^1H$, $^{13}C$ NMR; $^1H$—$^{13}C$ HMQC, HMBC and $^1H$—$^{15}N$ HMBC experiments (Table 4 below). The structure of 4 was similar to that of 3 with a C=O missing from the C-5 position.

The structures of 1 and 2 are similar to the structure of a known pyroglutamyl peptidase inhibitor pyrizinostatin. Pyrizinostatin has the same two-ring system (compound 3) but with a ketone side chain. Both 1 and 2 are optically active. It is possible that 1 and 2 are enantioselectively synthesized by the microorganism starting from 3 and 5. Direct analysis of fresh fermentation broth by HPLC showed that 1 and 2 naturally exist, while 3 was not observed (or below the detectable level). Upon storage, and during the isolation and purification process, decomposition predominates. The stability experiment showed that after incubating at 52° C. for 4 h, the amounts of 1 and 2 were reduced by 62% and 85%, respectively, in the aqueous solution. The formation of 3 was evidenced by HPLC analysis.

Formation of 5 was also confirmed by NMR. In a DMSO-$d_6$ solution of partially decomposed 1 or 2, free 5 was identified by the appearance of a proton at δ 3.60 and it correlates with carbon at δ 49.8 ($CH_2$) in HMQC experiment and with carbons at δ 187.4 and δ 173.0 in HMBC spectrum. 5 was purified by HPLC and converted to its HCl salt. The $^1H$ and $^{13}C$ NMR data of isolated 5 in its hydrochloric acid salt are identical to those of the synthetic one and comparable to those reported. With the structures of two degradation products (3 and 5) as additional proof, the structures of 1 and 2 are determined to be 4a-(2-amino-5-oxo-4,5-dihydro-3H-imidazol-4-yl)-2,4,4a,8-tetrahydro-2,6,8-trimethyl-pyrimido[5,4-e]-1,2,4-triazine-3,5,7(6H)-triones, and the structure of 4 is 2,5,7-trimethyl-2,7-dihydro-5H-imidazo[4,5-e]-1,2,4-triazine-3,6-dione.

Testing for PTP Inhibitory Activity

Compounds tested include 2-methylfervenulone, and several metabolites obtained when 2-methylfervenulone was isolated from IM 2096. In particular, the following were tested for PTP inhibitory activity:
4a-(2-Amino-5-oxo-4,5-dihydro-3H-imidazol-4-yl)-2,4,4a,8-tetrahydro-2,6,8-trimethyl-pyrimido[5,4-e]-1,2,4-triazine-3,5,7(6H)-triones (1 and 2).

(1): TFA salt. The salt contains TFA salt of 2, the ratio of 1:2 is 90.1:9.9 (by HPLC at 300 nm): yellow powder, $[\alpha]^{33}_D$−10.5 (c 1.0, MeOH); IR (KBr) 3380–3210 (br), 1783, 1724 (strong), 1676 (strong), 1540, 1440, 1382, 1203, 1139, 1024 cm$^{-1}$; UV (MeOH/$H_2O$/0.1% TFA, PDA) $\lambda_{max}$ 295 nm; Retention time (analytical HPLC) 14.3 min; NMR data, see Table 1 below.

TABLE 1

$^1H$, $^{13}C$ and $^{15}N$ NMR Data for (1).[a]

| No. | $^{13}C$ NMR | | $^1H$ NMR | | $^{15}N$ NMR[b] | |
| --- | --- | --- | --- | --- | --- | --- |
| | Base[c] | Salt[d] | Base[c] | Salt[d] | Base[c] | Salt[d] |
| N-1 | | | | | 285.3 | 286.0 |
| N2-CH$_3$ | 36.4 | 36.4 | 3.12 | 3.12 | 130.9 | 130.8 |
| 3 | 149.4 | 148.9 | | | | |
| N4-H | | | 7.46 | 8.17 | 81.3 | 77.4 |
| 4a | 60.6 | 60.4 | | | | |
| 5 | 164.3 | 162.9 | | | | |
| N6-CH$_3$ | 28.2 | 28.53 | 3.06 | 3.09 | 143.9 | 142.7 |
| 7 | 149.6 | 149.4 | | | | |
| N8-CH$_3$ | 30.2 | 30.4 | 3.09 | 3.17 | 108.7 | 107.4 |
| 8a | 134.8 | 133.3 | | | | |
| N-1' | | | | 10.13 | | |
| 2' | 173.0[e] | 160.6 | | | | |
| 2'-NH$_2$ | | | 7.17 | 9.14 | | 87.2 |
| | | | 7.85 | 9.43 | | |
| N-3' | | | 8.02 | 9.39 | 84.7 | 86.9 |
| 4' | 65.2 | 62.8 | 4.05 | 4.65 | | |
| 5' | 182.8 | 171.1 | | | | |

[a]Measured in DMSO-$d_6$ at 295K, all the $^1H$ peaks are singlets;
[b]Data obtained from HSQC and HMBC experiments;
[c]Base = neutral or free base;
[d]Salt = TFA salt;
[e]not visible in 1D
$^{13}C$ NMR, obtained from HMBC experiment.

(2): TFA salt. The salt contains TFA salt of 1, the ratio of 1:2 is 32.3:67.7 (by HPLC at 300 nm):yellow powder, $[\alpha]^{33}_D$+2.8 (c 1.0, MeOH); IR (KBr) 3390–3193 (br), 1785, 1724 (strong), 1676 (strong), 1540, 1441, 1382, 1203, 1139, 1024 cm$^{-1}$; UV (MeOH/$H_2O$/0.1% TFA, PDA) $\lambda_{max}$ 302 nm; Retention time (analytical HPLC) 13.3 min; NMR data, see Table 2 below; HRMS (ESI) m/z 323.1219 [calcd for $C_{11}H_{15}N_8O_4$ (M+H), 323.1216].

TABLE 2

$^1H$, $^{13}C$ and $^{15}N$ NMR Data for (2).[a]

| No. | $^{13}C$ NMR | | $^1H$ NMR | | $^{15}N$ NMR[b] | |
| --- | --- | --- | --- | --- | --- | --- |
| | Base[c] | Salt[d] | Base[c] | Salt[d] | Base[c] | Salt[d] |
| N-1 | | | | | 279.8 | 283.1 |
| N2-CH$_3$ | 36.4 | 36.4 | 3.13 | 3.13 | 132.1 | 130.8 |
| 3 | 150.3 | 149.3 | | | | |
| N4-H | | | 7.41 | 8.05 | 81.3 | 78.6 |
| 4a | 59.2 | 60.0 | | | | |

TABLE 2-continued $^1$H, $^{13}$C and $^{15}$N NMR Data for (2).[a]

| No. | $^{13}$C NMR Base[c] | $^{13}$C NMR Salt[d] | $^1$H NMR Base[c] | $^1$H NMR Salt[d] | $^{15}$N NMR[b] Base[c] | $^{15}$N NMR[b] Salt[d] |
|---|---|---|---|---|---|---|
| 5 | 162.9 | 161.9 | | | | |
| N6-CH$_3$ | 28.2 | 28.6 | 3.01 | 3.09 | 142.0 | 142.0 |
| 7 | 149.6 | 149.5 | | | | |
| N8-CH$_3$ | 29.9 | 30.2 | 3.15 | 3.17 | 111.0 | 109.1 |
| 0.33333 | 136.3 | 134.1 | | | | |
| N-1' | | | | 10.60 | | |
| 2' | 172.6[e] | 160.1 | | | | |
| 2'-NH$_2$ | | | 7.17 | 9.45 | | 87.0 |
| 8a | | | 7.85 | (3H) | | |
| N-3' | | | 8.02 | | 85.7 | |
| 4' | 64.4 | 63.5 | 4.169 | 4.72 | | |
| 5' | 183.2 | 170.5 | | | | |

[a,b,c,d,e]See footnotes of Table 1.

2,8-Dihydro-2,6,8-trimethyl-pyrimido(5,4-e]-1,2,4-triazine-3,5,7(6R)-trione (2-methylfervenulone (3): yellow solid; IR (KBr) 3568, 3536, 3435, 3380, 2963, 2935, 1728, 1694 (strong), 1666 (strong), 1615, 1541, 1473, 1437, 1385, 1328, 1312, 1247, 1032 cm$^{-1}$; UV (MeOH/H$_2$O/0.1% TFA, PDA) $\lambda_{max}$ 238, 417 nm; Retention time (analytical HPLC) 10.0 min; The NMR data are provided in Table 3 below.

TABLE 3

$^1$H, $^{13}$C and $^{15}$N NMR Data for (3) at 295K.

| No. | $^{13}$C NMR CDCl$_3$ | $^{13}$C NMR DMSO-d$_6$ | $^1$H NMR CDCl$_3$ | $^1$H NMR DMSO-d$_6$ | $^{15}$N NMR[a] CDCl$_3$ | $^{15}$N NMR[a] DMSO-d$_6$ |
|---|---|---|---|---|---|---|
| N-1 | | | | | 323.2 | 314.6 |
| N2-CH$_3$ | 42.1 | 41.2 | 3.91 | 3.74 | 187.3 | 181.9 |
| 3 | 150.8 | 152.6 | | | | |
| N-4 | | | | | — | — |
| 4a | 143.6 | 145.1 | | | | |
| 5 | 157.0 | 157.8 | | | | |
| N6-CH$_3$ | 29.7 | 28.7 | 3.51 | 3.33 | 155.3 | 152.6 |
| 7 | 148.9 | 149.2 | | | | |
| N8-CH$_3$ | 29.6 | 28.9 | 3.54 | 3.34 | 109.8 | 110.5 |
| 8a | 137.0 | 137.7 | | | | |

[a]Data obtained from HMBC experiments.

2,5,7-trimethyl-2,7-dihydro-5H-imidazo[4,5-e]-1,2,4-triazine-3,6-dione (4): pale yellow solid; IR (film) 3433, 1767, 1679, 1622, 1510, 1465, 1338, 1201, 1020 cm$^{-1}$; UV (MeOH/H$_2$O/0.1% TFA, PDA) $\lambda_{max}$ 260, 325 nm; Retention time (analytical HPLC) 11.0 min. The NMR data are provided in Table 4 below.

TABLE 4

$^1$H, $^{13}$C and $^{15}$N NMR Data for (4) at 295K.

| No. | $^{13}$C NMR CDCl$_3$ | $^{13}$C NMR DMSO-d$_6$ | $^1$H NMR CDCl$_3$ | $^1$H NMR DMSO-d$_6$ | $^{15}$N NMR[a] CDCl$_3$ | $^{15}$N NMR[a] DMSO-d$_6$ |
|---|---|---|---|---|---|---|
| N-1 | | | | | 293.3 | 288.1 |
| N2-CH$_3$ | 40.8 | 39.9 | 3.74 | 3.56 | 166.7 | 163.8 |
| 3 | 154.4 | 153.5 | | | | |
| N-4 | | | | | — | 231.9 |
| 4a | 150.2 | 150.6 | | | | |
| N5-CH$_3$ | 26.0 | 25.3 | 3.37 | 3.16 | 121.8 | 122.8 |
| 6 | 153.6 | 153.8 | | | | |
| N7-CH$_3$ | 26.1 | 25.7 | 3.34 | 3.163 | 105.2 | 106.5 |
| 7a | 133.3 | 134.0 | | | | |

[a]Data obtained from HMBC experiments.

Glycocyamidine (5) HCl salt. To the HPLC fraction of glycocyamidine, HCl (IN) was added to give 5 in the HCl salt form (5 mg): white solid, $^1$H NMR (DMSO-d$_6$) δ 12.20 (br s, 1H), 9.49 (s, 1H), 9.04 (br s, 1H), 8.82 (br s, 1H), 4.11 (s, 2H); $^{13}$C NMR (DMSO-d$_6$) δ 172.8, 158.5, 48.1; $^1$H—$^{13}$C HMQC δ$_H$ 4.11/δ$_c$ 48.1; $^1$H—$^{13}$C HMBC δ$_H$ 4.11/ δ$_c$ 172.8, 158.5. TFA salt: MS (ESI) m/z 122.0358 (calcd for M+Na, 122.0330), 199.0951 (calcd for 2M+H, 199.0943, +4.0 ppm), 221.0747 (calcd for 2M+Na, 221.0763). Its NMR spectra are identical to those of synthetic 5.HCl [obtained by refluxing the guanidineacetic acid with 6 N HCl for 6 days: $^1$H NMR (DMSO-d$_6$) δ 4.14 (s); $^{13}$C NMR (DMSO-d$_6$) δ 172.9, 159.0, 48.5] and comparable with those reported.

Bioassay showed that 3,2-methylfervenulone, is a potent PTP inhibitor (see below). 1 and 2 were much weaker inhibitors, but it was found by HPLC analysis that the extracts from IM 2096 containing 1 and 2 were contaminated with about 6-10% of 3. The TFA salts of 1 and 2 were further purified by washing with CH$_2$Cl$_2$ to remove trace amounts of 3. The fresh solution of 1 and 2 (TFA salt, the amount of 3 was estimated below 1 mole % by HPLC analysis) are inactive, but became active after prolonged storage. It is clear that 3 is responsible for the activity of 1 and 2.

The effects of 3 and 4 on the in vitro activities of several members of the PTP superfamily, representing receptor and non-receptor tyrosine-specific PTPs which utilize an active site cysteine in catalysis, were investigated. The results are shown in Table 5 below. At 1 μM, 3 inhibited all the PTPs tested, while 4, a proposed degradation product of 3, had negligible effects on PTP activity (Table 5). Although all receptor PTP catalytic domains (εD1D2, CD45, αD1D2, and LAR-D1) were inhibited to a similar extent (83–85%), the degree of inhibition exerted by 3 on the non-receptor PTPs tested was more variable, with about 65% inhibition observed for TC-PTP and 90% for Yop.

To examine whether 3 could inhibit the activity of phosphatases not belonging to the PTP superfamily, λPP, a dual specificity phosphatase closely related to the Type-1 and -2 serine/threonine phosphatases but with the ability also to dephosphorylate phosphotyrosyl proteins, and the non-specific alkaline phosphatase CIP were assayed in the presence and absence of compounds 3 and 4. While λPP activity was inhibited about 50% by 3, it was unaffected by 4. As shown by the comparative data in Table 5 below, neither compound had any detectable effect on the pNPP phosphatase activity of CIP. Reactions with CIP were performed at a neutral pH instead of a slightly acidic pH used in the measurements of the other enzymes. At this pH, while 3 has no effects on CIP activity, it continues to behave as a PTP inhibitor for both Yop and αD1D2 (results not shown), ruling out the possibility that the neutral environment plays a role in nullifying the inhibition by 3 on phosphatase activity. Thus the inhibitory action of 3 is specific to protein tyrosine phosphatases, but is not exclusive to those which employ an active site cysteine residue in their catalytic mechanism. In side-by-side reactions, 3 inhibited the PTPs to almost the same extent as the classical PTP inhibitor vanadate. The results of the activity shown by the proteins in the presence of 3 and 4 compared with sodium orthovanadate are shown in Table 5. The virtually indistinguishable effects of 3 and vanadate also extended to the dual specificity XPP, as well as to their lack of effect on CIP.

TABLE 5

Activities of protein phosphatases in the presence of 1 μM of compound 3 (2-methylfervenulone), 4 and sodium orthovanadate.

| Phosphatase | [nM] | 3 | 4 | $Na_3VO_4$ |
|---|---|---|---|---|
| Yop | 0.1 | 10 ± 1.0 | 95 ± 4.0 | 14 ± 1.0 |
| εD1D2 | 1.0 | 17 ± 4.0 | 99 ± 1.0 | 18 ± 2.0 |
| CD45 | 1.0 | 15 ± 2.5 | 96 ± 1.0 | 14 ± 0.5 |
| TCPTP | 1.0 | 34 ± 1.0 | 99 ± 2.0 | 31 ± 5.0 |
| αD1D2 | 5.0 | 17 ± 1.1 | 98 ± 0.5 | 24 ± 1.5 |
| LAR-D1 | 5.0 | 17 ± 2.0 | 97 ± 1.5 | 26 ± 1.0 |
| λPP | 5.0 | 48 ± 2.0 | 100 ± 6.0 | 49 ± 3.0 |
| CIP | 0.5 | 100 ± 1.0 | 99 ± 4.0 | 98 ± 3.0 |

Reactions were carried out as described in the Experimental Section. [nM] refers to the concentration of phosphatase assayed. The numbers indicate percentage activities relative to respective control reactions without addition of 3, 4, or $Na_3VO_4$. The numbers represent the average of the activities measured with three separate enzyme preparations, each of which was assayed in duplicate±S.D.

At 50 μM or 100 μM, 3 showed no antimicrobial activity against *Mycobacterium smegmatis, Staphylococcus aureus, Escherichia coli, Enterococcus faecalis, Proteus vulgaris, Pseudomonas aeruginosa, Candida albicans*, or *Curvualaria* sp.

The invention claimed is:

1. A compound which is 4a-(2-amino-5-oxo-4,5-dihydro-3H-imidazol-4-yl)-2,4,4a,8-tetrahydro-2,6,8-trimethyl-pyrimido[5,4-e]-1,2,4-triazine-3,5,7(6H)-trione or an acid addition salt thereof.

2. A pharmaceutical composition which comprises a pharmaceutically acceptable carrier or diluent and a compound as claimed in claim 1.

3. A method of treatment of type II diabetes which method comprises administering to a patient in need thereof an effective amount of a compound of formula (I):

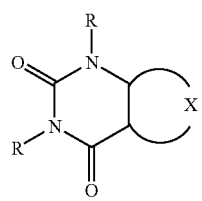

(I)

wherein
each R, which are the same or different, is H or $C_1$-$C_6$ alkyl, and
X completes a ring which is a substituted triazine having one of the following formulae (II) to (IV):

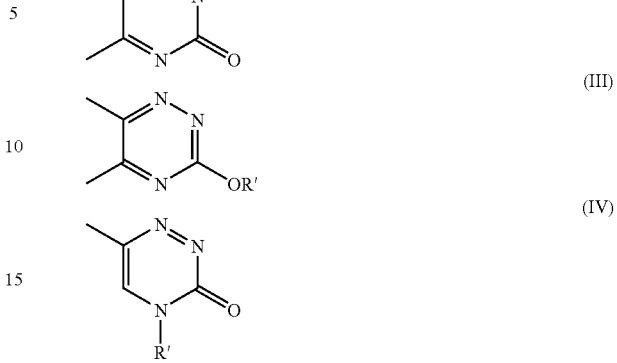

(II)

(III)

(IV)

wherein R' is H or $C_1$-$C_6$ alkyl;
or an enol tautomer of a compound of formula (I) in which any of the groups R or R' is hydrogen.

4. A method according to claim 3, wherein the compound of formula (I) has the following formula (Ia):

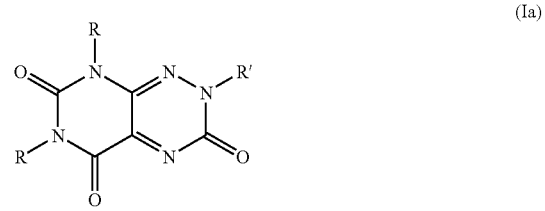

(Ia)

wherein R and R' are as defined in claim 3.

5. A method according to claim 3, wherein administration is via the intravenous route.

6. A method according to claims 3, wherein administration is oral administration.

7. A method of treatment of human breast cancer, human lung cancer, human colon carcinoma, rhabdomyosarcoma, osteogenic sarcoma or Ewing's sarcoma, which method comprises administering to a patient in need thereof an effective amount of the compound of claim 1 or an acid addition salt thereof.

8. A method of treatment of type II diabetes, which method comprises administering to a patient in need thereof an effective amount of the compound of claim 1 or an acid addition salt thereof.

* * * * *